(12) United States Patent
Kajiwara

(10) Patent No.: US 9,801,378 B2
(45) Date of Patent: Oct. 31, 2017

(54) METHOD OF CONTROLLING PEST

(71) Applicant: SUMITOMO CHEMICAL COMPANY, LIMITED, Tokyo (JP)

(72) Inventor: Yukari Kajiwara, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 31 days.

(21) Appl. No.: 14/739,713

(22) Filed: Jun. 15, 2015

(65) Prior Publication Data

US 2015/0272122 A1    Oct. 1, 2015

Related U.S. Application Data

(62) Division of application No. 13/716,303, filed on Dec. 17, 2012, now Pat. No. 9,084,426.

(30) Foreign Application Priority Data

Dec. 20, 2011  (JP) .................................. 2011-277958

(51) Int. Cl.
| | |
|---|---|
| A01N 43/56 | (2006.01) |
| A01N 43/653 | (2006.01) |
| A01N 43/54 | (2006.01) |
| A01N 41/10 | (2006.01) |
| A01N 43/84 | (2006.01) |
| A01N 33/22 | (2006.01) |
| A01N 37/28 | (2006.01) |

(52) U.S. Cl.
CPC ............. *A01N 43/84* (2013.01); *A01N 33/22* (2013.01); *A01N 37/28* (2013.01); *A01N 41/10* (2013.01); *A01N 43/54* (2013.01); *A01N 43/56* (2013.01); *A01N 43/653* (2013.01)

(58) Field of Classification Search
CPC ........ A01N 43/84; A01N 43/56; A01N 41/10; A01N 43/54; A01N 33/22; A01N 37/28; A01N 43/653

See application file for complete search history.

(56) References Cited

U.S. PATENT DOCUMENTS

| | | |
|---|---|---|
| 4,640,707 A | 2/1987 | Nagano et al. |
| 2005/0075372 A1 | 4/2005 | Lahm et al. |
| 2010/0317520 A1* | 12/2010 | Ikeda ................... A01N 43/653 504/130 |

* cited by examiner

*Primary Examiner* — John Pak
*Assistant Examiner* — Andriae M Holt
(74) *Attorney, Agent, or Firm* — Birch, Stewart, Kolasch & Birch, LLP

(57) ABSTRACT

Provided is a method which exerts an excellent effect in controlling a pest in a field of soybean, corn or cotton. A method of controlling a pest (weed, harmful arthropod) in a field of soybean, corn or cotton, including treating a field before, at or after seeding with a seed of soybean, corn or cotton treated with one or more diamide compounds, with one or more PPO-inhibiting compounds selected from the group consisting of flumioxazin, sulfentrazone, saflufenacil, oxyfluorfen, fomesafen, fomesafen sodium and a compound represented by the formula (I):

4 Claims, No Drawings

METHOD OF CONTROLLING PEST

CROSS-REFERENCE TO RELATED APPLICATIONS

This application is a Divisional of co-pending application Ser. No. 13/716,303 filed on Dec. 17, 2012, which claims priority under 35 U.S.C. §119(a) to Patent Application No. 2011-277958 filed in Japan on Dec. 20, 2011. All of the above applications are hereby expressly incorporated by reference into the present application.

BACKGROUND OF THE INVENTION

Field of the Invention

The present invention relates to a method of controlling a pest, namely, a harmful arthropod and a weed.

Description of the Related Art

A diamide compounds have been known as active ingredients of an insecticide. PPO-inhibiting compounds have been known as active ingredients of herbicides.

PRIOR ART LITERATURE

Patent Literature

Patent Literature 1: WO 02/066471
Patent Literature 2: WO 06/062978
Patent Literature 3: WO 08/072783

Non-Patent Literatures

Non-Patent Literature 1: Crop Protection Handbook, vol. 96 (2010)
Non-Patent Literature 2: Compendium of Pesticide Common Names (http://www.alanwood.net/pesticides/)

SUMMARY OF THE INVENTION

The present invention provides a method which exerts excellent effects in controlling a pest in a field of soybean, corn or cotton.

The present invention relates to the followings:

[1] A method of controlling a weed in a field of soybean, corn or cotton, comprising applying one or more PPO-inhibiting compounds selected from the group consisting of flumioxazin, sulfentrazone, saflufenacil, oxyfluorfen, fomesafen, fomesafen sodium and a compound represented by the formula (I):

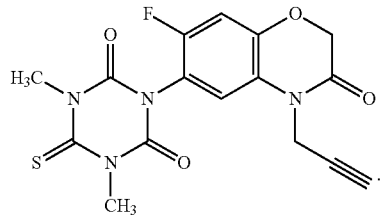

to a field before, at or after seeding with a seed of soybean, corn or cotton treated with one ore more diamide compounds.

[2] A method of controlling a pest in a field of soybean, corn or cotton, comprising steps of:

treating a seed of soybean, corn or cotton with one or more diamide compounds, and
treating a field before, at or after seeding with the seed of soybean, corn or cotton treated with the diamide compound, with one or more PPO-inhibiting compounds selected from the group consisting of flumioxazin, sulfentrazone, saflufenacil, oxyfluorfen, fomesafen, fomesafen sodium and a compound represented by the formula (I):

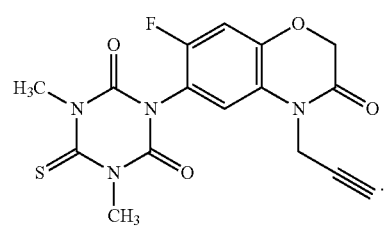

[3] The method of controlling a pest according to [1] or [2], wherein the diamide compound is selected from the group consisting of flubendiamide, chlorantraniliprole, a compound represented by the formula (II):

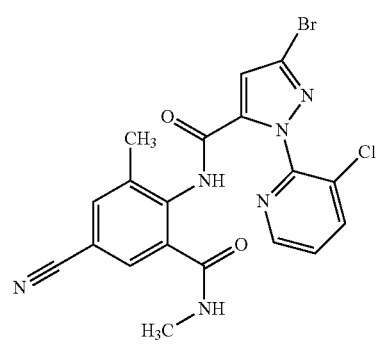

and a compound represented by the formula (III):

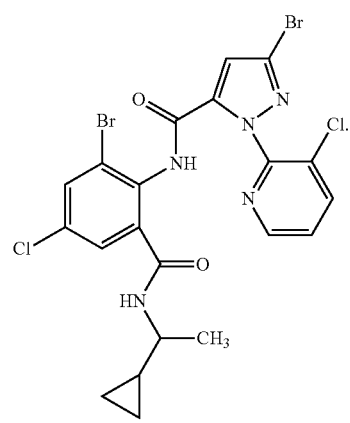

[4] The method of controlling a pest according to [1] or [2], wherein the diamide compound is chlorantraniliprole or a compound represented by the formula (II).

[5] The method of controlling a pest according to [3] or [4], wherein the PPO-inhibiting compound is flumioxazin.

[6] The method of controlling a pest according to [2], comprising a step of treating the field before seeding with the seed of soybean, corn or cotton, with the PPO-inhibiting compound.

[7] The method of controlling a pest according to [2], comprising a step of treating the field to be seeded, with the PPO-inhibiting compound simultaneously at seeding with the seed of soybean, corn or cotton.

[8] The method of controlling a pest according to [2], comprising a step of treating the field after seeding with the seed of soybean, corn or cotton, with the PPO-inhibiting compound.

[9] The method of controlling a pest according to [2], wherein the pest is a weed and/or a harmful arthropod.

[10] The method of controlling a pest according to [2], wherein the pest is a weed.

DETAILED DESCRIPTION OF THE PREFERRED EMBODIMENTS

The method of controlling a pest according to the present invention includes steps of:

(1) treating a seed of soybean, corn or cotton with one or more diamide compounds, and (2) treating a field before, at or after seeding with a seed of soybean, corn or cotton treated with one more diamide compounds, with one or more PPO-inhibiting compounds selected from the group consisting of flumioxazin, sulfentrazone, saflufenacil, oxyfluorfen, fomesafen, fomesafen sodium and a compound represented by the formula (I):

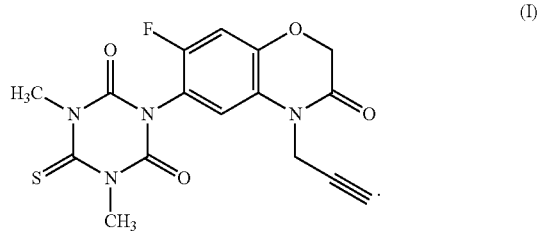 [SMILES: C#CCN1C(=O)COc2cc(F)c(-n3c(=O)n(C)c(=S)n(C)c3=O)cc21]

In the present invention, the seed of soybean, corn or cotton is not limited as far as it is a variety which is generally cultivated as a crop.

Examples of a plant of such a variety include plants to which resistance to a PPO inhibiting compound such as flumioxazin; a 4-hydroxyphenylpyruvate dioxygenase inhibiting compound such as isoxaflutole; an acetolactate synthase (hereinafter abbreviated as ALS) inhibiting compound such as imazethapyr or thifensulfuron methyl; a 5-enolpyruvylshikimate-3-phosphate synthase inhibiting compound such as glyphosate; a glutamine synthase inhibiting compound such as glufosinate; an auxin-type herbicide such as 2,4-D or dicamba; or bromoxynil has been imparted by a classical breeding method or a genetic engineering technique.

Examples of a crop to which resistance has been imparted by a classical breeding method include corn resistant to an imidazolinone-type ALS inhibiting herbicide such as imazethapyr, and this has already been commercially available under a trade name of Clearfield (registered trademark). Examples of such a crop also include STS soybean which is resistant to a sulfonylurea-type ALS inhibiting herbicide such as thifensulfuron methyl. Similarly, examples of a plant to which resistance to an acetyl CoA carboxylase-inhibiting compound such as trione oxime-type or aryloxyphenoxypropionic acid-type herbicide has been imparted by a classical breeding method include SR corn.

Examples of a plant to which resistance has been imparted by a genetic engineering technique include corn, soybean and cotton varieties which are resistant to glyphosate, and they have already been commercially available under trade names of RoundupReady (registered trademark), Agrisure (registered trademark)( GT, Gly-Tol (registered trademark) and the like. Similarly, there are corn, soybean and cotton varieties which are resistant to glufosinate by a genetic engineering technique, and they have already been commercially available under trade names of LibertyLink (registered trademark) and the like. There are corn and soybean varieties under the trade name of Optimum (registeredtrademark) and GAT (registered trademark), which are resistant to both of glyphosate and an ALS-inhibiting compound. Similarly, there are soybean varieties which are resistant to an imidazolinone-type ALS inhibiting compound by a genetic engineering technique, and this has been developed under the name of Cultivance. Similarly, there are cotton varieties which are resistant to bromoxynil by a genetic engineering technique, and this has already been commercially available under the trade name of BXN (registered trademark).

A crop such as a soybean which is resistant to dicamba can be produced by introducing a dicamba degrading enzyme such as dicamba monooxygenase isolated from *Pseudomonas maltophilia* into a plant (Behrens et al. 2007 Science 316: 1185-1188).

By introducing a gene encoding aryloxyalkanoate dioxygenase, a crop which becomes resistant to a phenoxy acid-type herbicide such as 2,4-D, MCPA, dichlorpropormecoprop, and an aryloxyphenoxypropionic acid-type herbicide such as quizalofop, haloxyfop, fluazifop, diclofop, fenoxaprop, metamifop, cyhalofop and clodinafop can be produced (Wright et al. 2010: Proceedings of National Academy of Science, 107 (47): 20240-20245).

The crop includes, for example, a crop which has become possible to synthesize a selective toxin known in *Bacillus* genus, using a genetic engineering technique.

Examples of the toxin which is expressed in such a genetically engineered plant include an insecticidal protein derived from *Bacillus cereus* or *Bacillus popilliae*; a δ-endotoxin such as Cry1Ab, Cry1Ac, Cry1F, Cry1Fa2, Cry2Ab, Cry3A, Cry3Bb1 or Cry9C, derived from *Bacillus thuringiensis*; an insecticidal protein such as VIP1, VIP2, VIP3 or VIP3A; an insecticidal protein derived from nematode; a toxin produced by an animal such as a scorpion toxin, a spider toxin, a bee toxin or an insect-specific neurotoxin; a filamentous fungus toxin; plant lectin; agglutinin; a protease inhibitor such as a trypsin inhibitor, a serine protease inhibitor, patatin, cystatin, and a papain inhibitor; a ribosome inactivating protein (RIP) such as lysine, corn-RIP, abrin, luffin, saporin or bryodin; a steroid metabolism enzyme such as 3-hydroxysteroid oxidase, ecdysteroid-UDP-glycosyl-transferase, and cholesterol oxidase; an ecdysone inhibitor; HMG-CoA reductase; an ion channel inhibitor such as a sodium channel inhibitor or a calcium channel inhibitor; juvenile hormone esterase; a diuretic hormone receptor; stilbene synthase; bibenzyl synthase; chitinase; glucanase; and the like.

A toxin expressed by such a genetically engineered crop includes a hybrid toxin of a δ-endotoxin protein such as Cry1Ab, Cry1Ac, Cry1F, Cry1Fa2, Cry2Ab, Cry3A, Cry3Bb1, Cry9C, Cry34Ab or Cry35Ab, and an insecticidal protein such as VIP1, VIP2, VIP3 or VIP3A, and a partially deleted toxin, and a modified toxin. The hybrid toxin can be produced by a new combination of different domains of these proteins using a genetic engineering technique. As the partially deleted toxin, Cry1Ab in which a part of an amino acid sequence has been deleted is known. In the modified toxin, one or a plurality of amino acids of a natural toxin are substituted. Examples of these toxins and recombinant plants which can synthesize these toxins are described in EP-A-0374753, WO 93/07273, WO 95/34656, EP-A-0427529, EP-A-451878, WO 03/052073 and the like. The toxins contained in these recombinant plans impart resistance to Coleoptera vermin, Diptera vermin and Lepidoptera vermin to a plant.

In addition, a genetically engineered plant containing one or a plurality of insecticidal vermin-resistant genes and expressing one or a plurality of toxins has already been known, and some of them are commercially available. Examples of these genetically engineered plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRI-SURE (registered trademark) CB Advantage (Bt11 corn borer (CB) trait), and Protecta (registered trademark).

In addition, genetically engineered cotton containing one or a plurality of insecticidal vermin-resistant genes and expressing one or a plurality of toxins have already been known, and some of them are commercially available. Examples of these genetically engineered cotton, include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton, variety expressing Cry1Ac and Cry1F toxins).

Examples of the plant used in the present invention also include plants to which resistance to an aphid, has been imparted, such as soybeans into which a Rag 1 (Resistance Aphid Gene 1) gene has been introduced.

The crop also includes a crop to which the ability to produce an anti-pathogenic substance having selective action has been imparted using a genetic engineering technique. As an example of the anti-pathogenic substance, a PR protein and the like are known (PRPs, EP-A-0392225). Such an anti-pathogenic substance and a genetically engineered plant producing the substance are described in EP-A-0392225, WO 95/33818, EP-A-0353191 and the like. Examples of the anti-pathogenic substance expressed in such a genetically engineered plant include an ion channel inhibitor such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and an anti-pathogenic substance generated by microorganisms, such as a peptide antibiotic, an antibiotic having a hetero ring, or a protein factor associated with resistance to plant diseases (which is called a plant disease-resistant gene and is described in WO 03/000906).

The crop also includes a plant to which a useful character such as oil cake component modification or an amino acid content enhancing character has been imparted using a genetic engineering technique. Examples thereof include VISTIVE (registered trademark) (low linolenic soybean having a reduced linolenic content) and high-lysine (high-oil) corn (corn having an increased lysine or oil content).

Further, stack varieties are also included in which a plurality of the classical herbicide character or herbicide-resistant gene, insecticidal vermin-resistant gene, anti-pathogenic substance production gene, and a useful character such as oil cake component modification or amino acid content enhancing character are combined.

The diamide compound acts on a calcium channel (ryanodine receptor) in a muscular cell of an insect to cause a calcium ion to be released, thereby, causing muscle constriction, and thus it rapidly stops the activity of the insect, leading the insect to death. Examples of the diamide compound include flubendiamide, chlorantraniliprole, a compound represented by the formula (II):

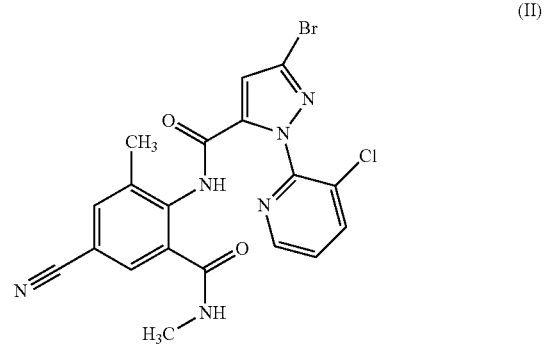 [SMILES: CNC(=O)c1cc(C#N)cc(C)c1NC(=O)c1cc(Br)nn1-c1ncccc1Cl]

(hereinafter, referred to as Compound 2) and a compound represented by the formula (III):

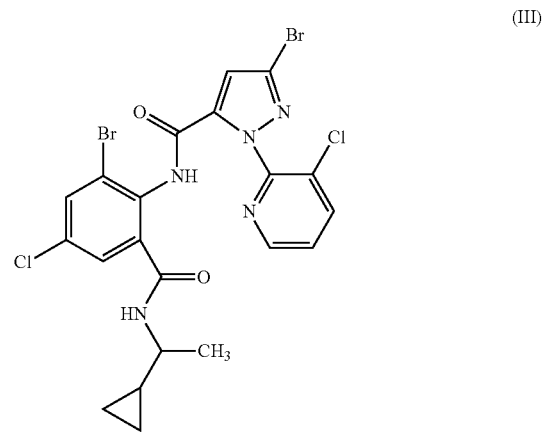 [SMILES: CC(NC(=O)c1cc(Cl)cc(Br)c1NC(=O)c1cc(Br)nn1-c1ncccc1Cl)C1CC1]

(hereinafter, referred to as Compound 3).

These diamide compounds are all known compounds, and flubendiamide and chlorantraniliprole can be used by purchasing commercially available preparations or standard products. Compound 2 is synthesized by the method described in WO 06/062978. Compound 3 is synthesized by the method described in WO 08/072783.

In the present invention, in the step of treating a seed of soybean, corn or cotton with the diamide compound, the diamide compound is usually mixed with a solid carrier or a liquid carrier, formulated with optional addition of an auxiliary agent for formulation, such as a surfactant, then used.

The diamide compound is applied at a dose in a range of usually 0.002 to 50 g, preferably 0.01 to 10 g, more preferably 0.05 to 2 g per 1 kg of the seed. Examples of a method of applying an active ingredient (i.e. diamide compound) to a seed of a plant include a method of covering a seed with a preparation containing an active ingredient; a method of immersing a seed in a preparation containing an active ingredient; and a method of coating a seed with a carrier containing an active ingredient.

In the present invention, there is a step of treating a field before, at or after seeding with a seed of soybean, corn or cotton treated with the diamide compound, with one or more PPO-inhibiting compounds.

The PPO-inhibiting compound is a herbicidally active compound which inhibits protoporphyrinogen IX oxidase (EC1.3.3.4) located on a chlorophyll synthesis pathway in a plastid of a plant and, as a result, leads to withering of the plant.

Examples of the PPO-inhibiting compound in the present invention include flumioxazin, sulfentrazone, saflufenacil, oxyfluorfen, fomesafen, fomesafen sodium and a compound represented by the formula (I):

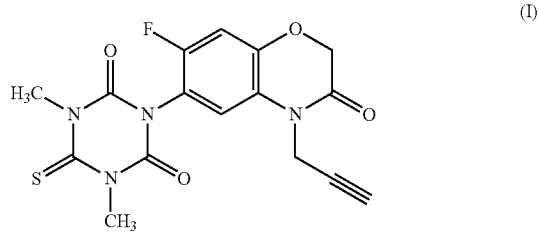 [SMILES: C#CCN1C(=O)COc2cc(F)c(-n3c(=O)n(C)c(=S)n(C)c3=O)cc21]

(hereinafter, referred to as Compound 1).

These PPO-inhibiting compounds are all known compounds, and Compound 1 is synthesized by the method described in 02/066471. Other compounds can be used by purchasing commercially available preparations or standard products.

In the step of treating the field with the PPO-inhibiting compound, the PPO-inhibiting compound is mixed with a solid carrier or a liquid carrier, formulated with optional addition of an auxiliary agent for formulation such as a surfactant, and used.

Examples of a method of treating the field with the PPO-inhibiting compound include a method of applying the PPO-inhibiting compound to a soil of the field and a method of applying the PPO-inhibiting compound to a weed after its emergence.

A does of the PPO-inhibiting compound used in the step of treating a field with the PPO-inhibiting compound is usually in the range of 5 to 5000 g per 10000 m$^2$, preferably 10 to 1000 g per 10000 m$^2$, more preferably 20 to 500 g per 10000 m$^2$. In the step of treating the field with the PPO-inhibiting compound, an adjuvant may be mixed upon treatment with the PPO-inhibiting compound.

The seed of soybean, corn or cotton treated with the diamide compound is seeded on a field by a conventional method. In the method of controlling a pest according to the present invention, the PPO-inhibiting compound may be applied before seeding with the seed of soybean, corn or cotton, may be applied simultaneously at seeding with the seed of soybean, corn or cotton or may be applied after seeding with the seed of soybean, corn, or cotton.

When a field is treated with the PPO-inhibiting compound before seeding with the soybean seed or the corn seed, the field is treated with the PPO-inhibiting compound 50 days before seeding to immediately before seeding, preferably 30 days before seeding to immediately before seeding, further preferably 20 days before seeding to immediately before seeding.

When a field is treated with the PPO-inhibiting compound after seeding with the soybean seed or the corn seed, the field is treated with the PPO-inhibiting compound preferably immediately after seeding to 50 days after seeding, more preferably immediately after seeding to 3 days after seeding. Examples of a specific treatment term when a field is treated with the PPO-inhibiting compound after seeding with the soybean seed include a term from preemergence to flowering of the soybean. Among preemergence to flowering of the soybean, preferred is a from preemergence to 6 compound leaves of the soybean, further preferred is a term from preemergence to 3 compound leaves of the soybean. A specific treating term when a field is treated with the PPO-inhibiting compound after seeding with the corn seed is from preemergence to 12 leaves of corn, preferably a term from, preemergence to 8 leaves of corn, further preferably a term from preemergence to 6 leaves of corn. In addition, a leaf age of corn is determined by the Leaf Collar Method.

When a field is treated with the PPO-inhibiting compound before seeding with the cotton seed, the field is treated with the PPO-inhibiting compound 50 days before seeding to immediately before seeding, preferably 30 days before seeding to immediately before seeding, further preferably 20 days before seeding to immediately before seeding.

When a field is treated with the PPO-inhibiting compound after seeding with the cotton seed, the field is treated with the PPO-inhibiting compound immediately after seeding to 70 days after seeding, preferably 30 days after seeding to 50 days after seeding. Examples of a specific treating term when a field is treated with the PPO-inhibiting compound after seeding with the cotton seed include preemergence to flowering of the cotton. Preferred is a lignification initiation term of the stem base of the cotton to a term when a lignification portion is 20 cm from the base.

According to the method of controlling a pest of the present invention, pests such as harmful arthropods and/or weeds in a field of soybean, corn or cotton can be controlled without causing significant phototoxicity on a crop.

Examples of the harmful arthropod include the followings:

Hemiptera vermin: Delphacidae such as *Laodelphax striatellus, Nilaparvata lugens*, and *Sogatella furcifera*; Deltocephalidae such as *Nephotettix cincticeps* and *Nephotettix virescens*; Aphididae such as *Aphis gossypii, Myzus persicae, Brevicoryne brassicae, Macrosiphum euphorbiae, Aulacorthum solani, Rhopalosiphum padi*, and *Toxoptera citricidus*; Pentatomidae such as *Nezara antennata, Riptortus clavetus, Leptocorisa chinensis, Eysarcoris parvus, Halyomorpha mista*, and *Lygus lineolaris*; Aleyrodidae such as *Trialeurodes vaporariorum, Bemisia tabaci*, and *Bemisia argentifolii*; Coccidae such as *Aonidiella aurantii, Comstockaspis perniciosa, Unaspis citri, Ceroplastes rubens*, and *Icerya purchasi*; Tingidae; Psyllidae; and the like;

Lepidoptera vermin: Pyralidae such as *Chilo suppressalis, Tryporyza incertulas, Cnaphalocrocis medinalis, Notarcha derogata, Plodia interpunctella, Ostrinia furnacalis, Ostrinia nubilaris, Hellula undalis*, and *Pediasia teterrellus*; Noctuidae such as *Spodoptera litura, Spodoptera exigua, Pseudaletia separata, Mamestra brassicae, Agrotis ipsilon, Plusia nigrisigna, Trichoplusia* spp., *Heliothis* spp., and

*Helicoverpa* spp.; Pieridae such as *Pieris rapae*; Adoxophyes spp.; Tortricidae such as *Grapholita molesta, Leguminivora glycinivorella, Matsumuraeses azukivora, Adoxophyes orana fasciata, Adoxophyes* sp., *Homona magnanima, Archips fuscocupreanus*, and *Cydia pomonella*; Gracillariidae such as *Caloptilia theivora* and *Phyllonorycter ringoneella*; Carposinidae such as *Carposina niponensis*; Lyonetiidae such, as *Lyonetia* spp.; Lymantriidae such as *Lymantriidae* spp. and *Euproctis* spp.; Yponameutidae such as *Plutella xylostella*, Gelechiidae such as *Pectinophora gossypiella* and *Phthorimaea operculella*; Arctiidae such as *Hyphantria cunea*; Tineidae such as *Tinea translucens* and *Tineola bisselliella*; and the like;

Thysanoptera vermin: Thripidae such as *Frankliniella occidentalis, Thrips parmi, Scirtothrips dorsalis, Thrips tabaci, Frankliniella intonsa*, and *Frankliniella fusca*;

Diptera vermin: Agromyzidae such as *Musca domestica, Culex popiens pallens, Tabanus trigonus, Hylemya antiqua, Hylemya platura, Anopheles sinensis, Agromyza oryzae, Hydrellia griseola, Chlorops oryzae*, and *Liriomyza trifolii*; *Dacus cucurbitae, Ceratitis capitata*, and the like;

Coleoptera vermin: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*, and the like;

Orthoptera vermin: *Locusta migratoria, Gryllotalpa africana, Oxya yezoensis, Oxya japonica*, and the like;

Hymenoptera vermin: *Athalia rosae, Acromyrmex* spp., *Solenopsis* spp., and the like;

Blattidae vermin: *Blattella germanica, Periplaneta fuliginosa, Periplaneta americana, Periplaneta brunnea, Blatta orientalis*, and the like;

Acarina vermin: Tetranychidae such as *Tetranychus urticae, Panonychus citri*, and *Oligonychus* spp.; Eriophyidae such as *Aculops pelekassi*; Tarsonemidae such as *Polyphagotarsonemus latus*; Tenuipalpidae; Tuckerellidae; Acaridae such as *Tyrophagus putrescentiae*; Dermanyssidae such as *Dermatophagoides farinae* and *Dermatophagoides ptrenyssnus*; Cheyletidae such as *Cheyletus eruditus, Cheyletus malaccensis*, and *Cheyletus moorei*; and the like.

Examples of the weed include; the followings:

Urticaceae weeds: *Urtica urens*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*

Portulacaceae weeds: *Portulaca oleracea*

Caryophyllaceae weeds: *Stellaria media, Cerastium holosteoides, Cerastium glomeratum, Spergula arvensis, Silene gallica*

Aizoaceae weeds: *Mollugo verticillata*

Chenopodiaceae weeds: *Chenopodium album, Chenopodium ambrosioides, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*

Papaveraceae weeds: *Papaver rhoeas, Argemone mexicana*

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus*

Capparaceae weeds: *Cleome affinis*

Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*

Oxalidaceae weeds: *Oxalis corniculata, Oxalis strica, Oxalis oxyptera*

Geraniaceae weeds: *Geranium carolinense, Erodium cicutarium*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*

Malvaceae weeds: *Abutilon theophrasti, Sida rhombifolia, Sida cordifolia, Sida spinosa, Sida glaziovii, Sida santaremnensis, Hibiscus trionum, Anoda cristata, Malvastrum coromandelianum*

Sterculiaceae weeds: *Waltheria indica*

Violaceae weeds: *Viola arvensis, Viola tricolor*

Cucurbitaceae weeds: *Sicyos angulatus, Echinocystis lobata, Momordica charantia*

Lythraceae weeds: *Lythrum salicaria*

Apiaceae weeds: *Hydrocotyle sibthorpioides*

Sapindaceae weeds: *Cardiospermum halicacabum*

Primulaceae weeds: *Anagallis arvensis*

Asclepiadaceae weeds: *Asclepias syriaca, Ampelamus albidus*

Rubiaceae weeds: *Galium aparine, Galium spurium* var. *echinospermon, Spermacoce latifolia, Richardia brasiliensis, Borreria alata*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*

Boraginaceae weeds: *Myosotis arvensis*

Lamiaceae weeds: *Lamium purpureum, Lamium amplexicaule, Leonotis nepetaefolia, Hyptis suaveolens, Hyptis lophanta, Leonurus sibiricus, Stachys arvensis*

Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*

Scrophulariaceae weeds: *Veronica hederaefolia, Veronica persica, Veronica arvensis*

Plantaginaceae weeds: *Plantago asiatica*

Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardio-*

*spermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis*

Liliaceae weeds: *Allium canadense, Allium vineale*

Commelinaceae weeds: *Commelina communis, Commelina bengharensis, Commelina erecta*

Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spicaventi, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*

Cyperaceae weeds: *Cyperus microiria, Cyperus iria, Cyperus odoratus, Cyperus rotundus, Cyperus esculentus, Kyllinga gracillima*

Equisetaceae weeds: *Equisetum arvense, Equisetum palustre*, and the like.

In the method of controlling a pest of the present invention, one or more kinds of other agrochemicals can be also used in combination simultaneously with, or separately from the diamide compound or the PPO inhibiting compound. Examples of the other agrochemicals include an insecticidal agent, a miticide, a nematicide, a fungicide, a herbicide, a plant growth regulating agent and a safener.

Examples of the herbicide, the plant growth regulating agent and the safener include the followings:

Herbicide: dicamba and a salt thereof (diglycolamine salt, dimethylammonium salt, isopropylammonium salt, potassium salt, sodium salt, choline salt), 2,4-D and a salt or ester thereof (butotyl ester, dimethylammonium salt, diolamine salt, ethylhexyl ester, isooctyl ester, isopropylammonium salt, sodium salt, triisopropanolamine salt, choline salt), 2,4-DB and a salt or ester thereof (dimethylammonium salt, isooctyl ester, choline salt), MCPA and a salt, or ester thereof (dimethylammonium salt, 2-ethylhexyl ester, isooctyl ester, sodium salt, choline salt), MCPB, mecoprop and a salt or ester thereof (dimethylammonium salt, diolamine salt, ethadyl ester, 2-ethylhexyl ester, isooctyl ester, methyl ester, potassium salt, sodium salt, trolamine salt, choline salt), mecoprop-P and a salt or ester thereof (dimethylammonium salt, 2-ethylhexyl ester, isobutyl salt, potassium salt, choline salt), dichlorprop and a salt or ester thereof (butotyl ester, dimethylammonium salt, 2-ethylhexyl ester, isooctyl ester, methyl ester, potassium salt, sodium salt, choline salt), dichlorprop-P, dichlorprop-P-dimethylammonium, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triazifalm, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, bennzobicyclon, dithiopyr, triclopyr and a salt or ester thereof (butotyl ester, triethylammonium salt), fluroxypyr, fluroxypyr-meptyl, thiazopyr, aminopyralid and a salt thereof (potassium salt, triisopropanolammonium salt, choline salt), clopyralid and a salt thereof (olamine salt, potassium salt, triethylammonium salt, choline salt), picloram and a salt thereof (potassium salt, triisopropanolammonium salt, choline salt), dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazapyr-ammonium, imazaquin, imazaquin-ammonium, imazethapyr, imazethapyr-ammonium, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glyphosate-guanidine, glufosinate, glufosinate-ammonium, glufosinate-P, glufosinate-P-sodium, bialafos, anilofos, bensulide, butamifos, paraquat, paraquat-dichloride, diquate and diquat-dipromide Plant growth regulating agents: hymexazol, paclobutrazol, uniconazole, uniconazole-P, inabenfide, prohexadione-calcium, 1-methylcyclopropene, trinexapac and gibberellins.

Safeners: benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride and oxabetrinil.

EXAMPLES

The present invention will be described below by way of examples, but the present invention is not limited to these examples.

First, evaluation criteria of insecticidal activity, herbicidal activity and phytotoxicity on a crop shown in the following examples will be shown.

[Insecticidal Activity]

For evaluating the insecticidal activity, life or death of an insect at investigation is determined, and a controlling value is obtained by the following equation:

Controlling value (%)=100×(1−T/C)

Letters in the equation represent the following meanings.
C: Number of insects at observation of non-treated section
T: Number of insects at observation of treated-section

[Herbicidal Activity and Phytotoxicity on Crop]

Evaluation of herbicidal activity is classified into 0 to 100, letting no or little difference when the state of germination or growth of a test weed at investigation is compared with that of non-treatment to be "0", and letting withering of a test plant or complete inhibition of germination or growth to be "100".

For evaluation of phytotoxicity on a crop, when phytotoxicity is hardly perceived, it is represented by "no damage", when slight phytotoxicity is perceived, it is represented by "slight", when moderate phytotoxicity is perceived, it is represented by "moderate", and when severe phytotoxicity is perceived, it is represented by "severe".

Example 1

Pre-plant Application in Cotton

In combinations shown in Table 1, insecticidal activity, herbicidal activity, and phytotoxicity on a crop are confirmed according to the aforementioned criteria, by the following method.

A soil is packed into a pot, a weed is seeded, and the soil surface is uniformly treated with a PPO inhibiting compound. After 15 days, cotton seeds with a diamide compound attached thereto are seeded. This pot is placed in a greenhouse. Fifteen days after seeding, the insecticidal activity, the herbicidal activity and the phytotoxicity on a crop are investigated.

TABLE 1

| Combination | Diamide compound | PPO inhibiting compound |
|---|---|---|
| 1-1 | Flubendiamide | Flumioxazin |
| 1-2 | Chlorantraniliprole | Flumioxazin |
| 1-3 | Compound 2 | Flumioxazin |
| 1-4 | Compound 3 | Flumioxazin |
| 1-5 | Flubendiamide | Fomesafen |
| 1-6 | Chlorantraniliprole | Fomesafen |
| 1-7 | Compound 2 | Fomesafen |
| 1-8 | Compound 3 | Fomesafen |
| 1-9 | Flubendiamide | Fomesafen sodium |
| 1-10 | Chlorantraniliprole | Fomesafen sodium |
| 1-11 | Compound 2 | Fomesafen sodium |
| 1-12 | Compound 3 | Fomesafen sodium |
| 1-13 | Flubendiamide | Oxyfluorfen |
| 1-14 | Chlorantraniliprole | Oxyfluorfen |
| 1-15 | Compound 2 | Oxyflourfen |
| 1-16 | Compound 3 | Oxyfluorfen |
| 1-17 | Flubendiamide | Saflufenacil |
| 1-18 | Chlorantraniliprole | Saflufenacil |
| 1-19 | Compound 2 | Saflufenacil |
| 1-20 | Compound 3 | Saflufenacil |
| 1-21 | Flubendiamide | Sulfentrazone |
| 1-22 | Chlorantraniliprole | Sulfentrazone |
| 1-23 | Compound 2 | Sulfentrazone |
| 1-24 | Compound 3 | Sulfentrazone |
| 1-25 | Flubendiamide | Compound 1 |
| 1-26 | Chlorantraniliprole | Compound 1 |
| 1-27 | Compound 2 | Compound 1 |
| 1-28 | Compound 3 | Compound 1 |

Example 2

Post-directed Application in Cotton

In combinations shown in Table 2, insecticidal activity, herbicidal activity and phytotoxicity on a crop are confirmed according to the aforementioned criteria, by the following method.

A diamide compound is attached to each of cotton seeds. Then, the seeds are seeded on a cultivated land. Thirty days after seeding, in the state where the main stem of cotton is lignified 15 cm from the ground surface, the cultivated land is subjected to Post-directed application with a PPO inhibiting compound. Twenty eight days after treatment, the insecticidal activity, the herbicidal activity and the phototoxicity on a crop are investigated.

TABLE 2

| Combination | Diamide compound | PPO inhibiting compound |
|---|---|---|
| 2-1 | Flubendiamide | Flumioxazin |
| 2-2 | Chlorantraniliprole | Flumioxazin |
| 2-3 | Compound 2 | Flumioxazin |
| 2-4 | Compound 3 | Flumioxazin |
| 2-5 | Flubendiamide | Fomesafen |
| 2-6 | Chlorantraniliprole | Fomesafen |
| 2-7 | Compound 2 | Fomesafen |
| 2-8 | Compound 3 | Fomesafen |
| 2-9 | Flubendiamide | Fomesafen sodium |
| 2-10 | Chlorantraniliprole | Fompsafen sodium |
| 2-11 | Compound 2 | Fomesafen sodium |
| 2-12 | Compound 3 | Fomesafen sodium |
| 2-13 | Flubendiamide | Oxyfluorfen |
| 2-14 | Chlorantraniliprole | Oxyfluorfen |
| 2-15 | Compound 2 | Oxyfluorfen |
| 2-16 | Compound 3 | Oxyfluorfen |
| 2-17 | Flubendiamide | Saflufenacil |
| 2-18 | Chlorantraniliprole | Saflufenacil |
| 2-19 | Compound 2 | Saflufenacil |
| 2-20 | Compound 3 | Saflufenacil |
| 2-21 | Flubendiamide | Sulfentrazone |
| 2-22 | Chlorantraniliprole | Sulfentrazone |
| 2-23 | Compound 2 | Sulfentrazone |
| 2-24 | Compound 3 | Sulfentrazone |
| 2-25 | Flubendiamide | Compound 1 |
| 2-26 | Chlorantraniliprole | Compound 1 |
| 2-27 | Compound 2 | Compound 1 |
| 2-28 | Compound 3 | Compound 1 |

Example 3

Pre-plant Application in Soybean

In combinations shown in Table 3, insecticidal activity, herbicidal activity and phytotoxicity on a crop are confirmed according to the aforementioned criteria, by the following method.

A sort is packed in a pot, a weed is seeded, and the soil surface is uniformly treated with a PPO inhibiting compound. After 7 days, soybean seeds with a diamide compound attached thereto are seeded. This pot is placed in a greenhouse. Fifteen day after seeding, the insecticidal activity, the herbicidal activity and the phytotoxicity on a crop are investigated.

TABLE 3

| Combination | Diamide compound | PPO inhibiting compound |
|---|---|---|
| 3-1 | Flubendiamide | Flumioxazin |
| 3-2 | Chlorantraniliprole | Flumioxazin |
| 3-3 | Compound 2 | Flumioxazin |
| 3-4 | Compound 3 | Flumioxazin |
| 3-5 | Flubendiamide | Fomesafen |
| 3-6 | Chlorantraniliprole | Fomesafen |
| 3-7 | Compound 2 | Fomesafen |
| 3-8 | Compound 3 | Fomesafen |
| 3-9 | Flubendiamide | Fomesafen sodium |
| 3-10 | Chlorantraniliprole | Fomesafen sodium |
| 3-11 | Compound 2 | Fomesafen sodium |
| 3-12 | Compound 3 | Fomesafen sodium |
| 3-13 | Flubendiamide | Saflufenacil |
| 3-14 | Chlorantraniliprole | Saflufenacil |
| 3-15 | Compound 2 | Saflufenacil |
| 3-16 | Compound 3 | Saflufenacil |
| 3-17 | Flubendiamide | Oxyfluorfen |
| 3-18 | Chlorantraniliprole | Oxyfluorfen |
| 3-19 | Compound 2 | Oxyfluorfen |
| 3-20 | Compound 3 | Oxyfluorfen |
| 3-21 | Flubendiamide | Compound 1 |
| 3-22 | Chlorantraniliprole | Compound 1 |
| 3-23 | Compound 2 | Compound 1 |
| 3-24 | Compound 3 | Compound 1 |
| 3-25 | Flubendiamide | Sulfentrazone |
| 3-26 | Chlorantraniliprole | Sulfentrazone |
| 3-27 | Compound 2 | Sulfentrazone |
| 3-28 | Compound 3 | Sulfentrazone |

Example 4

Preemergence Application in Soybean

In combinations shown in Table 4, insecticidal activity, herbicidal activity and phytotoxicity on a crop are confirmed according to the aforementioned criteria, by the following method.

A diamide compound is attached to each of soybean seeds. Then, a soil is packed into a pot, and the seeds and a seed of a weed are seeded. On the day of the seeding, the soil surface is uniformly treated with a PPO inhibiting compound. This pot is placed in a greenhouse. Fifteen days after seeding, the insecticidal activity, the herbicidal activity and the phytotoxicity on a crop are investigated.

TABLE 4

| Combination | Diamide compound | PPO inhibiting compound |
|---|---|---|
| 4-1 | Flubendiamide | Flumioxazin |
| 4-2 | Chlorantraniliprole | Flumioxazin |
| 4-3 | Compound 2 | Flumioxazin |
| 4-4 | Compound 3 | Flumioxazin |
| 4-5 | Flubendiamide | Fomesafen |
| 4-6 | Chlorantraniliprole | Fomesafen |
| 4-7 | Compound 2 | Fomesafen |
| 4-8 | Compound 3 | Fomesafen |
| 4-9 | Flubendiamide | Fomesafen sodium |
| 4-10 | Chlorantraniliprole | Fompsafen sodium |
| 4-11 | Compound 2 | Fomesafen sodium |
| 4-12 | Compound 3 | Fomesafen sodium |
| 4-13 | Flubendiamide | Saflufenacil |
| 4-14 | Chlorantraniliprole | Saflufenacil |
| 4-15 | Compound 2 | Saflufenacil |
| 4-16 | Compound 3 | Saflufenacil |
| 4-17 | Flubendiamide | Compound 1 |
| 4-18 | Chlorantraniliprole | Compound 1 |
| 4-19 | Compound 2 | Compound 1 |

TABLE 4-continued

| Combination | Diamide compound | PPO inhibiting compound |
|---|---|---|
| 4-20 | Compound 3 | Compound 1 |
| 4-21 | Flubendiamide | Sulfentrazone |
| 4-22 | Chlorantraniliprole | Sulfentrazone |
| 4-23 | Compound 2 | Sulfentrazone |
| 4-24 | Compound 3 | Sulfentrazone |

Example 5

Preemergence Application in Corn

In combinations shown in Table 5, insecticidal activity, herbicidal activity and phytotoxicity on a crop are confirmed according to the aforementioned criteria, by the following method.

A diamide compound is attached to each of corn seeds. Then, a soil is packed into a pot, and the seeds and a seed of a weed are seeded. On the day of the seeding, the soil surface is uniformly treated with a PPO inhibiting compound. This pot is placed in a greenhouse. Fifteen days after the seeding, the insecticidal activity, the herbicidal activity and the phytotoxicity on a crop are investigated.

TABLE 5

| Combination | Diamide compound | PPO inhibiting compound |
|---|---|---|
| 5-1 | Flubendiamide | Saflufenacil |
| 5-2 | Chlorantraniliprole | Saflufenacil |
| 5-3 | Compound 2 | Saflufenacil |
| 5-4 | Compound 3 | Saflufenacil |
| 5-5 | Flubendiamide | Compound 1 |
| 5-6 | Chlorantraniliprole | Compound 1 |
| 5-7 | Compound 2 | Compound 1 |
| 5-8 | Compound 3 | Compound 1 |

Example 6

Pre-plant Application in Corn

In combinations shown in Table 6, insecticidal activity, herbicidal activity and phototoxicity on a crop are confirmed according to the aforementioned criteria, by the following method.

A soil is packed into a pot, a weed is seeded, and the soil surface is uniformly treated with a PPO inhibiting compound. After 7 days, corn seeds with a diamide compound attached thereto are seeded. This pot is placed in a greenhouse. Fifteenth days after the seeding, the insecticidal activity, the herbicidal activity and the phototoxicity on a crop are investigated.

TABLE 6

| Combination | Diamide compound | PPO inhibiting compound |
|---|---|---|
| 6-1 | Flubendiamide | Flumioxazin |
| 6-2 | Chlorantraniliprole | Flumioxazin |
| 6-3 | Compound 2 | Flumioxazin |
| 6-4 | Compound 3 | Flumioxazin |
| 6-5 | Flubendiamide | Saflufenacil |
| 6-6 | Chlorantraniliprole | Saflufenacil |
| 6-7 | Compound 2 | Saflufenacil |
| 6-8 | Compound 3 | Saflufenacil |
| 6-9 | Flubendiamide | Compound 1 |
| 6-10 | Chlorantraniliprole | Compound 1 |
| 6-11 | Compound 2 | Compound 1 |
| 6-12 | Compound 3 | Compound 1 |

According to the method of controlling a pest of the present invention, a pest in a field of soybean, corn or cotton can be effectively controlled.

What is claimed is:

1. A method of controlling a weed in a field of soybean, corn or cotton, comprising steps of:

treating a seed of soybean, corn or cotton with one or more diamide compounds selected from the group consisting of chlorantraniliprole and a compound represented by the formula (II):

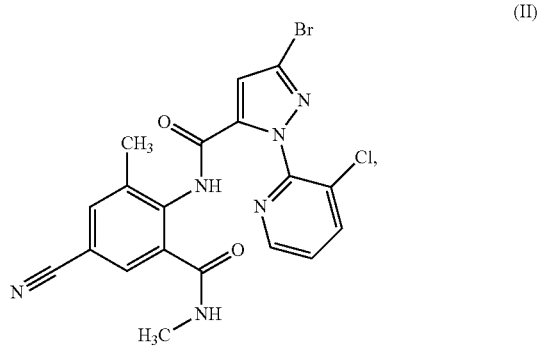 [SMILES: CNC(=O)c1cc(C#N)cc(C)c1NC(=O)c1cc(Br)nn1-c1ncccc1Cl]

and treating the field before, at or after seeding with the seed of soybean, corn or cotton treated with the diamide compound, with one or more PPO-inhibiting compounds selected from the group consisting of sulfentrazone, saflufenacil and fomesafen sodium; wherein the amount of the diamide compound is 0.01 to 2 g per 1 kg of seeds, and the amount of the PPO-inhibiting compound is 10 to 1000 g per 10000 $m^2$.

2. The method of controlling a weed according to claim 1, comprising a step of treating the field before seeding with the seed of soybean, corn or cotton, with the PPO-inhibiting compound; wherein the amount of the diamide compound is 0.01 to 2 g, per 1 kg of seeds, and the amount of the PPO-inhibiting compound is 10 to 1000 g per 10000 $m^2$.

3. The method of controlling a weed according to claim 1, comprising a step of treating the field to be seeded, with the PPO-inhibiting compound simultaneously at seeding with the seed of soybean, corn or cotton; wherein the amount of the diamide compound is 0.01 to 2 g, per 1 kg of seeds, and the amount of the PPO-inhibiting compound is 10 to 1000 g per 10000 $m^2$.

4. The method of controlling a weed according to claim 1, comprising a step of treating the field after seeding with the seed of soybean, corn or cotton, with the PPO-inhibiting compound; wherein the amount of the diamide compound is 0.01 to 2 g per 1 kg of seeds, and the amount of the PPO-inhibiting compound is 10 to 1000 g per 10000 $m^2$.

* * * * *